(12) United States Patent
Kellnberger et al.

(10) Patent No.: US 11,896,347 B2
(45) Date of Patent: Feb. 13, 2024

(54) OPTICAL WAVEGUIDE FOR GENERATING ULTRASONIC WAVES

(71) Applicant: Siemens Healthcare GmbH, Erlangen (DE)

(72) Inventors: Stephan Kellnberger, Erlangen (DE); Oliver Schmidt, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/462,165

(22) Filed: Aug. 31, 2021

(65) Prior Publication Data
US 2022/0079451 A1 Mar. 17, 2022

(30) Foreign Application Priority Data

Sep. 11, 2020 (DE) ...................... 10 2020 211 441.2

(51) Int. Cl.
*A61B 5/00* (2006.01)
*A61B 8/00* (2006.01)
(Continued)

(52) U.S. Cl.
CPC .............. *A61B 5/0095* (2013.01); *A61B 8/54* (2013.01); *G01N 21/1702* (2013.01); *G02B 6/02076* (2013.01)

(58) Field of Classification Search
CPC ....... A61B 5/0095; A61B 8/54; A61B 6/5252; A61B 8/08; A61B 8/4416; A61B 8/4444;
(Continued)

(56) References Cited

U.S. PATENT DOCUMENTS 6,100,969 A 8/2000 Perez
6,539,135 B1 * 3/2003 Canning ................ G02B 6/105
385/11
(Continued)

FOREIGN PATENT DOCUMENTS

CN 1643413 A 7/2005
CN 101990417 A 3/2011
(Continued)

OTHER PUBLICATIONS

Wissmeyer, G. et. al., "Looking at sound: optoacoustics with all-optical ultrasound detection", Light: Science & Applications vol. 7, Article No. 53, 2018.
(Continued)

*Primary Examiner* — Yi-Shan Yang
*Assistant Examiner* — Kaitlyn E Sebastian
(74) *Attorney, Agent, or Firm* — Harness, Dickey & Pierce, P.L.C.

(57) ABSTRACT

An optical waveguide-transmitter apparatus, an ultrasonic transceiver apparatus, an ultrasonic imaging apparatus and an associated production method are disclosed. The optical waveguide-transmitter apparatus includes a substrate made of a semiconductor material; a carrier layer arranged on the substrate; and at least one transmitter-optical waveguide made of a semiconductor material with a refractive index greater than a refractive index of the carrier layer. At least one side of the waveguide is at least partially surrounded by the carrier layer. The waveguide is configured at an end facing toward the examination region for a decoupling of the light beams into the examination region for generating the ultrasonic waves in the examination region by way of the decoupled light beams for an optoacoustic imaging and/or has, on the end facing toward the examination region, an
(Continued)

optical absorption layer for such a conversion of the light beams.

25 Claims, 5 Drawing Sheets

(51) Int. Cl.
*G01N 21/17* (2006.01)
*G02B 6/02* (2006.01)

(58) Field of Classification Search
CPC ..... A61B 8/4488; A61B 8/4494; A61B 6/502; A61B 6/4417; A61B 6/00; A61B 8/4483; A61B 5/055; G01N 21/1702; G02B 6/02076; G02B 2006/12097; G02B 2006/12107; G02B 2006/12138; G02B 6/122; G02B 6/124; G03B 42/06
See application file for complete search history.

(56) References Cited

U.S. PATENT DOCUMENTS

| | | | |
|---|---|---|---|
| 10,670,804 B1* | 6/2020 | Bian | G02B 6/1223 |
| 2001/0042410 A1 | 11/2001 | Ogawa | |
| 2002/0006145 A1* | 1/2002 | Evans | B82Y 20/00 372/50.12 |
| 2005/0089262 A1 | 4/2005 | Jenkins et al. | |
| 2009/0285523 A1 | 11/2009 | Dubois et al. | |
| 2010/0268058 A1 | 10/2010 | Chen | |
| 2012/0271170 A1 | 10/2012 | Emelianov et al. | |
| 2013/0303909 A1 | 11/2013 | Kang et al. | |
| 2014/0005556 A1 | 1/2014 | Hirota et al. | |
| 2014/0114187 A1* | 4/2014 | Rozental | G01H 9/004 600/407 |
| 2014/0360273 A1 | 12/2014 | Zhang et al. | |
| 2017/0079622 A1 | 3/2017 | O'Donnell et al. | |
| 2018/0028117 A1* | 2/2018 | Desjardins | A61B 8/461 |
| 2018/0310831 A1* | 11/2018 | Cheng | G01N 33/48 |

FOREIGN PATENT DOCUMENTS

| | | |
|---|---|---|
| CN | 102437510 A | 5/2012 |
| CN | 103687545 A | 3/2014 |
| CN | 104334088 A | 2/2015 |
| CN | 104375231 A | 2/2015 |
| CN | 106328751 A | 2/2017 |
| CN | 109141493 A | 1/2019 |
| DE | 102017213753 A1 | 2/2019 |
| KR | 20100049287 A | 5/2010 |
| KR | 20180077966 A | 7/2018 |
| WO | WO 0019243 A1 | 4/2000 |
| WO | WO 2019170884 A1 | 9/2019 |
| WO | WO 2019239148 A1 | 12/2019 |
| WO | WO 2020039436 A1 | 2/2020 |

OTHER PUBLICATIONS

Fraunhofer Institute for Biomedical Engineering, "Improved biopsies with MRI-compatible ultrasound system", DiPhAS KoMBUS: an MR-compatible, 256-channel ultrasound system, https:/www.ibmt.fraunhofer.de/en/ibmt-press-releases/press-KoMBUS-2019-11-01.html, 2019.

Rebling, J. et. al.; "Integrated catheter for simultaneous radiofrequency ablation and optoacoustic monitoring of lesion progression —In: Optics Letters"; vol. 43; Apr. 15, 2018; No. 8; S. 021116 (2014); pp. 1886-1889.

Wang, C. et. al., "Monitoring of the central blood pressure waveform via a conformal ultrasonic device", Nature Biomedical Engineering vol. 2, pp. 687-695, 2018.

Taruttis, A. et. al. ; "Optoacoustic imaging of human Vasculature: Feasibility by Using a Handheld Probe"; In: Radiology; vol. 281; RSNA; Oct. 2016; No. 1; pp. 256-263.

Shaiderman, R. et. al., "Sub-micron silicon-on-insulator resonator for ultrasound detection", arXiv:1902.04115.

Rosenthal, A. et. al., "Embedded ultrasound sensor in a silicon-on-insulator photonic platform", Appl. Phys. Lett. 104, 021116, Jan. 2014.

Lan, L. et. al .; "A fiber optoacoustic guide with augmented reality for precision breast-conserving surgery"; In: Light: Science & Applications (2018) 7:2; pp. 1-11.

Butterflynetwork, Ultrasound, ultra-simplified, Butterfly IQ, https://www.butterflynetwork.com/, Stand: Jul. 2, 2020.

German Office Action dated May 6, 2021.

Leinders S.M. et al. : A sensitive optical micro-machined ultrasound sensor (OMUS) based on a silicon photonic ring resonator on an acoustical membrane*, Scientific Reports, Sep. 22, 2015.

\* cited by examiner

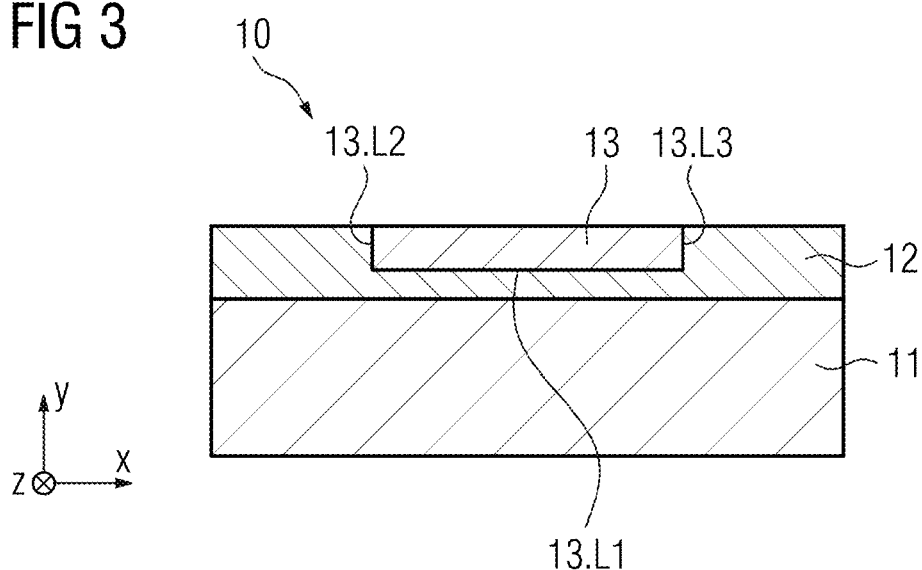
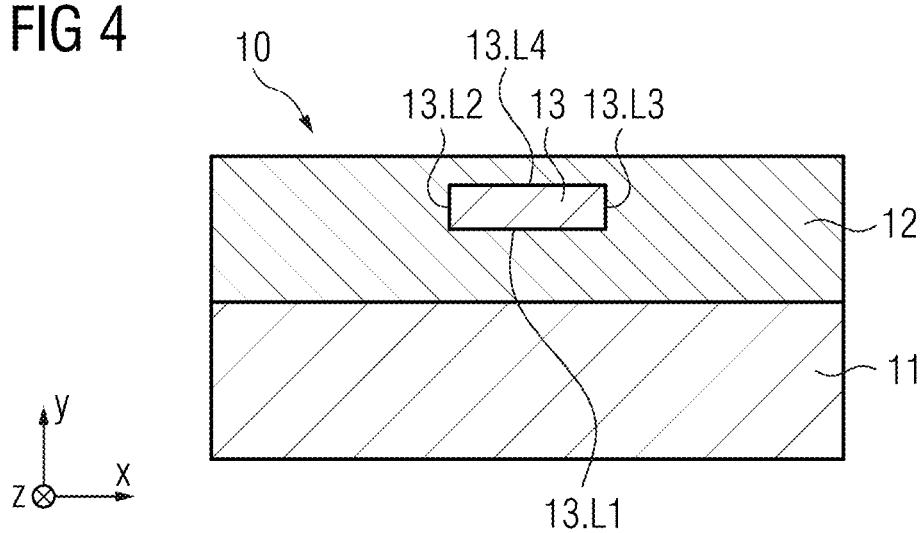

OPTICAL WAVEGUIDE FOR GENERATING ULTRASONIC WAVES

PRIORITY STATEMENT

The present application hereby claims priority under 35 U.S.C. § 119 to German patent application number DE 102020211441.2 filed Sep. 11, 2020, the entire contents of which are hereby incorporated herein by reference.

FIELD

Example embodiments of the invention generally relate to an optical waveguide-transmitter apparatus, an ultrasonic transceiver apparatus, an ultrasonic imaging apparatus and an associated production method.

BACKGROUND

Ultrasonic imaging via an ultrasonic imaging apparatus advantageously enables a visualization of an anatomical or morphological body structure of a patient. In ultrasonic imaging, typically, non-ionizing ultrasonic waves are used in order to be able to generate at least one typically multidimensional medical image of the patient. The ultrasonic waves typically have a frequency of more than 100 kHz.

In principle, a conventional ultrasonic imaging apparatus has an ultrasonic transmitter apparatus or an ultrasonic receiver apparatus. The ultrasonic waves can be generated by the ultrasonic transmitter apparatus and transmitted into an examination region. At the ultrasonic receiver apparatus, the ultrasonic waves from the examination region can be detected. The ultrasonic transmitter apparatus can have a plurality of ultrasonic transmitter elements for generating the ultrasonic waves. The ultrasonic receiver apparatus typically has a plurality of ultrasonic receiver elements for detecting the ultrasonic waves. If the conventional ultrasonic imaging apparatus has the ultrasonic transmitter apparatus and the ultrasonic receiver apparatus, the ultrasonic transmitter apparatus and the ultrasonic receiver apparatus can be integrated into an ultrasonic transceiver apparatus. In this case, therefore, ultrasonic waves are emitted by the ultrasonic transceiver apparatus into the examination region, absorbed and/or reflected there, for example, by an examination object and the reflected ultrasonic waves are detected at the ultrasonic transceiver apparatus. For example, a conventional ultrasonic probe and/or an ultrasonic head is such an ultrasonic transceiver apparatus. It is conceivable that the ultrasonic transmitter elements correspond to the ultrasonic receiver elements such that these ultrasonic transceiver elements can typically generate and detect the ultrasonic waves alternatingly.

Some other imaging apparatuses, in particular, a magnetic resonance tomograph or a computed tomography system place specific requirements on the ultrasonic imaging apparatus when the ultrasonic imaging apparatus is to be operated in close proximity to the other imaging apparatus, in order to ensure an electromagnetic compatibility between the different imaging apparatuses. In particular, an ultrasonic imaging apparatus that is operated in close proximity to the magnetic resonance tomograph is preferably non-ferromagnetic and/or, in particular, free from conducting materials, in order to prevent the induction of eddy currents.

A generation and/or a detection of the ultrasonic waves can be based upon a piezoelectric effect according to which electrical signals can be converted into mechanical sound waves and/or mechanical sound waves can be converted into electrical signals. The mechanical sound waves typically have a frequency such that they can be referred to as ultrasonic waves. Alternatively, ultrasonic waves can be generated and/or detected via a CMUT (capacitive micromachined ultrasonic transducer) technology. The CMUT technology is based upon changes in an electrical capacitance dependent upon the mechanical sound waves and/or ultrasonic waves. From the scientific publication "Monitoring of the central blood pressure waveform via a conformal ultrasonic device", by Wang et. al, Nat Biomed Eng. Sep. 2018; 2(9): 687-695, published online Sep. 11, 2018, doi: 10.1038/s41551-018-0287-x, there is known a portable ultrasonic transceiver apparatus with typically a plurality of conventional piezoelectric ultrasonic transceiver elements and/or CMUT ultrasonic transceiver elements which preferably enable an areal contact with the patient. Piezoelectric and/or CMUT ultrasonic transceiver elements can be produced with a size of less than 100 μm through the use of silicon substrates.

A sensitivity of the ultrasonic transceiver elements typically depends upon the extent of an active region of the respective ultrasonic transceiver element. Typically, the smaller the extent, the lower the sensitivity becomes. A middle frequency and a detection bandwidth, inter alia, are characteristic of an ultrasonic transceiver element. The middle frequency is typically defined as the frequency component with the greatest sensitivity and/or the peak frequency. The central frequency can alternatively also be referred to as the center frequency. The detection bandwidth is typically defined as the frequency band in the spectrum between the lower and upper detection frequency with an amplitude of −6 dB. In general, the principle applies that a resolution of a conventional ultrasonic transceiver element is typically better the higher is the upper −6 dB detection frequency. In addition, it is assumed in general that the more structures that have to be resolved, the broader is the detection bandwidth. Piezoelectric ultrasonic transceiver elements and/or CMUT ultrasonic transceiver elements typically have relatively low central frequencies of less than 100 MHz or even less than 50 MHz with a limited detection bandwidth of approximately 50-80%. Typically, the thinner the piezoelectric transceiver elements are, the higher is the frequency of the ultrasonic waves.

From the scientific publication "Embedded ultrasound sensor in a silicon-on-insulator photonic platform", Rosenthal et al., Appl. Phys. Lett. 104, 021116 (2014), https://doi.org/10.1063/1.4860983, there is known, for example, an ultrasonic receiver apparatus comprising a silicon substrate and an optical waveguide with a n-phase displaced Bragg grating, wherein ultrasonic waves are detected via laser beam pulse interferometry. An effectiveness of this silicon ultrasonic receiver apparatus is described, for example, in the scientific publication "Sub-micron silicon-on-insulator resonator for ultrasound detection", by Shnaiderman et al., arXiv preprint arXiv:1902.04115, 2019, wherein in this case, the ultrasonic waves are generated by the examination object itself in accordance with the optoacoustic effect by excitation with laser beams provided by a separate external laser. The ultrasonic waves generated in accordance with the optoacoustic effect can be detected, in particular, via the laser beam pulse interferometry occurring in the optical waveguide, according to which an imaging method of this type uses substantially optical methods. An optoacoustic imaging method of this type enables an enhanced signal-to-noise ratio as compared with conventional piezoelectric or CMUT transceiver elements and typically a higher detection bandwidth, see Wissmeyer et al. "Looking at sound: optoacoustics with all-optical ultrasound detection", Light Sci Appl 7, 53 (2018), https://doi.org/10.1038/s41377-018-0036-7. It is usually a further advantage that the above described silicon ultrasonic receiver apparatus typically needs no electrical cabling, whereby advantageously, no electromagnetic interference fields are generated.

However, a conventional piezoelectric ultrasonic transceiver apparatus or a CMUT ultrasonic transceiver apparatus typically has electrical cabling and can thus be such an apparatus that does not have any or has no unrestricted compatibility with the other imaging apparatus. The operation of a conventional ultrasonic transceiver apparatus in close proximity to the magnetic resonance tomograph can therefore negatively influence an imaging in the magnetic resonance tomograph. In particular, a high level of sensitivity of the magnetic resonance tomograph due to the pulse and/or echo ultrasonic waves of the conventional ultrasonic transceiver apparatus can be degraded so that typically a dedicated screening is necessary between the two apparatuses. Accordingly, an operation of a conventional (piezoelectric or CMUT) ultrasonic transceiver apparatus with such an electrical cabling in close proximity to the other imaging apparatus is often not possible. An ultrasonic imaging apparatus presented by the Fraunhofer Institute for Biomedical Engineering, IBMT has an ultrasonic transceiver apparatus that is compatible with magnetic resonance tomography systems.

SUMMARY

Embodiments of the invention provide an optical waveguide-transmitter apparatus, an ultrasonic transceiver apparatus, an ultrasonic imaging apparatus and an associated production method with a small structure and a low electromagnetic fault susceptibility.

Advantageous embodiments are disclosed in the claims.

The optical waveguide-transmitter apparatus according to at least one embodiment of the invention for imaging an examination region via ultrasonic waves generated by light beams, comprises:
  a substrate made of a semiconductor material,
  a carrier layer arranged on the substrate, and
  at least one transmitter-optical waveguide made of a semiconductor material with a refractive index greater than a refractive index of the carrier layer, wherein at least one longitudinal side of the at least one transmitter-optical waveguide is at least partially surrounded by the carrier layer, wherein the at least one transmitter-optical waveguide is configured for guiding the light beams, wherein the at least one transmitter-optical waveguide is configured at an end facing toward the examination region for a decoupling of the light beams into the examination region for generating the ultrasonic waves in the examination region via the decoupled light beams for an optoacoustic imaging, and/or wherein the at least one transmitter-optical waveguide has, on the end facing toward the examination region, an optical absorption layer for such a conversion of the light beams, so that in the examination region the generated ultrasonic waves are decoupled for an ultrasonic imaging process.

The ultrasonic transceiver apparatus according to at least one embodiment of the invention comprises the optical waveguide-transmitter apparatus and an ultrasonic receiver-optical waveguide for receiving ultrasonic waves reflected in the examination region, wherein at least one longitudinal side of the ultrasonic receiver-optical waveguide is at least partially surrounded by the carrier layer of the optical waveguide-transmitter apparatus. This embodiment is particularly advantageous since an integration of the at least one transmitter-optical waveguide and of the ultrasonic receiver-optical waveguide is enabled on the carrier layer, in particular, on the "semiconductor material on an insulator" platform.

An ultrasonic imaging apparatus according to at least one embodiment of the invention comprises the optical waveguide-transmitter apparatus or the ultrasonic transceiver apparatus, a control apparatus and a light source apparatus, wherein the light source apparatus is connected via at least one fiber to the at least one transmitter-optical waveguide and wherein the control apparatus is configured for an actuation of the light source apparatus such that the at least one transmitter-optical waveguide guides the light beams during operation. The light source apparatus can comprise an LED or a laser. The at least one fiber can be a glass fiber. The at least one fiber is, for example, attached to a second end of the at least one transmitter-optical waveguide, the end lying opposite the end facing toward the examination region, for example, via an interface, in particular, via an optical coupler and/or via the multiplexer.

An inventive method of at least one embodiment is for producing the optical waveguide-transmitter apparatus comprises, wherein a substrate made of a semiconductor material is provided, a carrier layer is arranged on the substrate and at least one transmitter-optical waveguide is mounted on the carrier layer such that at least one longitudinal side of the at least one transmitter-optical waveguide is at least partially surrounded by the carrier layer. In the manufacturing method, for example, a wafer is processed via ultraviolet radiation or electron-beam lithography such that the at least one optical waveguide can guide the light beams in the optical waveguide-transmitter apparatus.

At least one embodiment of the invention is directed to an optical waveguide-transmitter apparatus for imaging an examination region via ultrasonic waves generated by light beams, comprising:
  a substrate including a semiconductor material;
  a carrier layer, arranged on the substrate; and
  at least one transmitter-optical waveguide including a semiconductor material with a refractive index greater than a refractive index of the carrier layer, at least one longitudinal side of the at least one transmitter-optical waveguide being at least partially surrounded by the carrier layer,
  wherein the at least one transmitter-optical waveguide is configured to guide the light beams, and
  wherein at least one of
    the at least one transmitter-optical waveguide is configured, at an end facing toward the examination region, for a decoupling of the light beams into the examination region for generating the ultrasonic waves in the examination region by way of the decoupled light beams for an optoacoustic imaging, and
    the at least one transmitter-optical waveguide includes, on the end facing toward the examination region, an optical absorption layer for conversion of the light beams to decouple, in the examination region, the ultrasonic waves generated for an ultrasonic imaging process.

At least one embodiment of the invention is directed to an ultrasonic transceiver apparatus, comprising:
  the optical waveguide-transmitter apparatus of an embodiment; and an ultrasonic receiver-optical waveguide to receive ultrasonic waves reflected in the examination region, wherein at least one longitudinal side of the ultrasonic receiver-optical waveguide is at least partially surrounded by the carrier layer of the optical waveguide-transmitter apparatus.

At least one embodiment of the invention is directed to an ultrasonic imaging apparatus, comprising:

the ultrasonic transceiver apparatus of an embodiment;
a control apparatus; and
a light source apparatus, connected via at least one fiber to the at least one transmitter-optical waveguide and
wherein the control apparatus is configured to actuate the light source apparatus to enable the at least one transmitter-optical waveguide to guide the light beams during operation.

At least one embodiment of the invention is directed to a method for producing an optical waveguide-transmitter apparatus, comprising:

providing a substrate including a semiconductor material;
arranging a carrier layer on the substrate; and mounting at least one transmitter-optical waveguide on the carrier layer such that at least one longitudinal side of the at least one transmitter-optical waveguide is at least partially surrounded by the carrier layer At least one embodiment of the invention is directed to the method of an embodiment, wherein the at least one transmitter-optical waveguide is configured to guide the light beams, and wherein at least one of
the at least one transmitter-optical waveguide is configured, at an end facing toward the examination region, for a decoupling of the light beams into the examination region for generating the ultrasonic waves in the examination region by way of the decoupled light beams for an optoacoustic imaging, and
the at least one transmitter-optical waveguide includes, on the end facing toward the examination region, an optical absorption layer for conversion of the light beams to decouple, in the examination region, the ultrasonic waves generated for an ultrasonic imaging process.

BRIEF DESCRIPTION OF THE DRAWINGS

The invention will now be described and explained in greater detail making reference to the example embodiments illustrated in the drawings. In principle, structures and units which remain essentially the same are identified in the following description of the figures with the same reference characters as on the first occurrence of the relevant structure or unit.

In the drawings:

FIGS. 1 to 4 are different embodiments of a cross-section of the optical waveguide-transmitter apparatus 10.

DETAILED DESCRIPTION OF THE EXAMPLE EMBODIMENTS

Figure 1:
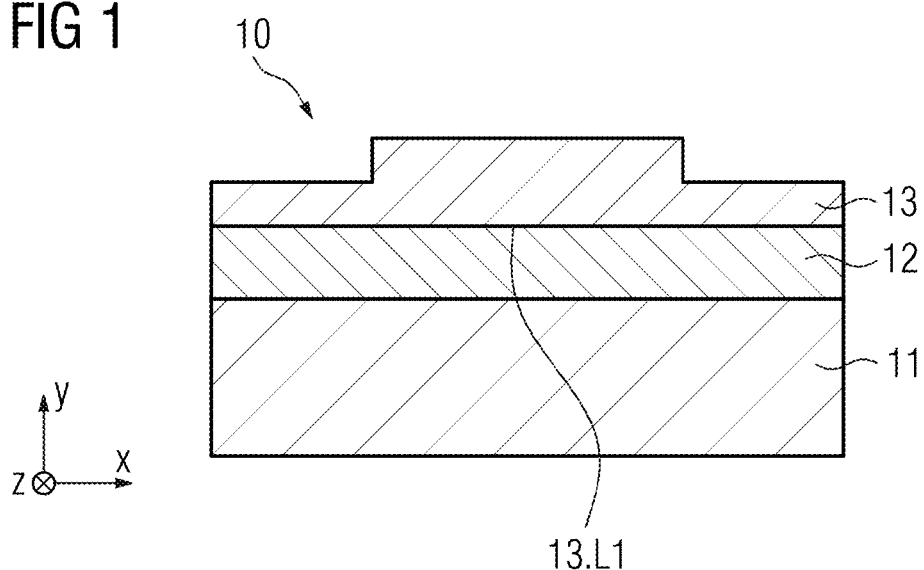

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The optical waveguide-transmitter apparatus according to at least one embodiment of the invention for imaging an examination region via ultrasonic waves generated by light beams, comprises:
- a substrate made of a semiconductor material,
- a carrier layer arranged on the substrate, and
- at least one transmitter-optical waveguide made of a semiconductor material with a refractive index greater than a refractive index of the carrier layer, wherein at least one longitudinal side of the at least one transmitter-optical waveguide is at least partially surrounded by the carrier layer, wherein the at least one transmitter-optical waveguide is configured for guiding the light beams, wherein the at least one transmitter-optical waveguide is configured at an end facing toward the examination region for a decoupling of the light beams into the examination region for generating the ultrasonic waves in the examination region via the decoupled light beams for an optoacoustic imaging, and/or wherein the at least one transmitter-optical waveguide has, on the end facing toward the examination region, an optical absorption layer for such a conversion of the light beams, so that in the examination region the generated ultrasonic waves are decoupled for an ultrasonic imaging process.

The construction of the optical waveguide-transmitter apparatus with the substrate, the carrier layer and the at least one transmitter-optical waveguide advantageously has a small structure as compared with conventional ultrasonic probes. The small structure is achieved, in particular, in that over the past years, continuous further developments have taken place in the field of semiconductor production. These further developments have lead, in particular, to a miniaturization of the semiconductor structures produced and advantageously enable the optical waveguide-transmitter apparatus with the small structure. The construction of the optical waveguide-transmitter apparatus with the semiconductor preferably enables an economical integration into an imaging apparatus since the conventional, in particular, metal oxide-based semiconductor production can be made use of, whereby preferably widely used production possibilities exist and/or a combination with further semiconductor structures such as a CMUT structure is possible without difficulty.

The at least one optical waveguide can have, for example, a rectangular cross-section in or below the micrometer range. For example, the rectangular cross-section of the at least one optical waveguide is less than 100 μm×50 μm, advantageously less than 10 μm×5 μm, particularly advantageously less than 1 μm×0.5 μm. The at least one optical waveguide can be, in the context of the invention, a "single-mode" optical waveguide and/or a "multi-mode" optical waveguide. By means, in particular, of the dimensioning of the rectangular cross-section of the optical waveguide, an intensity distribution of the light in the optical waveguide is determined. The "single-mode" optical waveguide typically has a rectangular cross-section that is smaller than a rectangular cross-section of the "multi-mode" optical waveguide. In the "single-mode" optical waveguide, typically only one mode is supported and the light distribution in the "single-mode" optical waveguide is distributed, for example, in a Gaussian form. If the rectangular cross-section of the optical waveguide is enlarged, then, usually, higher modes can propagate. Typically thereby, more light can be transported, but the intensity distribution is less well defined. The light beams can be conducted continuously or pulsed in the at least one optical waveguide. The guidance of the light beams includes transportation of the light beams in the optical waveguide.

Technically regarded, the optical waveguide-transmitter apparatus can be associated with a photonics system. The semiconductor photonics system described comprises, in particular, advantages with regard to a high level of integration density and/or a monolithic integration. The optical waveguide-transmitter apparatus has, advantageously for the photonics, a high refractive index difference between the material of the at least one transmitter-optical waveguide and the material of the carrier layer. By this means, a restriction and a narrow guidance of the light beams in the at least one transmitter-optical waveguide with the small structure in or below the micrometer range advantageously is possible.

Advantageously, the optical waveguide-transmitter apparatus has no electrical cabling, whereby advantageously, no electromagnetic interference fields are created or coupled in. The optical waveguide-transmitter apparatus is preferably a purely optical ("all optical") waveguide-transmitter apparatus. An arrangement of the optical waveguide-transmitter apparatus in relatively close proximity to a magnetic resonance tomograph, for example, in the main magnetic field of the magnetic resonance tomograph or within a bore of the magnetic resonance tomograph is therefore advantageously possible while ensuring electromagnetic compatibility. A further advantage can be that the optical waveguide-transmitter apparatus can be arranged in an X-ray beam path of an X-ray device without electrical cabling absorbing X-ray radiation. A variant according to the invention relates to the arrangement of the optical waveguide-transmitter apparatus in the main magnetic field of the magnetic resonance tomograph or in the X-ray ray path of the X-ray device.

The substrate is, in particular, a substrate layer on which the carrier layer is arranged. The carrier layer is arranged, in particular, between the substrate and the at least one optical waveguide. The carrier layer is, in particular, an insulating layer which separates the at least one optical waveguide from the substrate. The optical waveguide-transmitter apparatus therefore uses a conventional "semiconductor on an insulator" platform. The carrier layer comprises, in particular, silicon dioxide or consists of silicon dioxide.

The semiconductor material comprises, in particular, silicon, germanium, gallium, phosphorus, Ti:LiNbO$_3$ and/or antimony. Ti:LiNbO$_3$ is a material specifically for optical waveguides, wherein titanium is diffused into LiNbO$_3$. Advantageously, the semiconductor material comprises silicon, germanium, gallium, phosphorus, Ti:LiNbO$_3$ and/or antimony. The semiconductor material of the substrate can correspond to the semiconductor material of the at least one optical waveguide.

The imaging is, in particular, a medical imaging. A patient is typically situated in the examination region. Typically provided between the patient and the optical waveguide-transmitter apparatus is a medium that is as far as possible gas-free, for example, an ultrasonic gel on the basis of water for reflection-free conduction of the ultrasonic waves between the patient and the at least one transmitter-optical waveguide.

The at least one transmitter-optical waveguide consists, in particular, of the semiconductor material with the refractive index greater than the refractive index of the carrier layer. The at least one transmitter-optical waveguide can guide the light waves, in particular, because the at least one longitudinal side of the at least one transmitter-optical waveguide is at least partially surrounded by the carrier layer. In other words, the carrier layer and the semiconductor material of the at least one transmitter-optical waveguide cooperate in such a way that light beams can preferably propagate almost without loss in the at least one transmitter-optical waveguide. The at least one longitudinal side is typically parallel to the optical axis of the at least one transmitter-optical waveguide. The optical axis typically corresponds to a propagation direction of the light beams in an optical waveguide. The at least one longitudinal side is thus surrounded by the carrier layer such that the carrier layer touches the at least one longitudinal side in a contact region and, in particular, adjoins the at least one longitudinal side. The at least one longitudinal side of the at least one transmitter-optical waveguide can be at least partially embedded in the carrier layer. At least partially surrounded or embedded means, in particular, that in particular a longitudinal portion of the longitudinal side of the at least one transmitter-optical waveguide touches or adjoins the carrier layer. It is conceivable, in principle, that the at least one longitudinal side is surrounded over the whole length by the carrier layer. The at least one transmitter-optical waveguide is surrounded, in addition to the carrier layer, by the substrate typically over a comparable length.

The optoacoustic imaging defines, in particular, the variant of the optical waveguide-transmitter apparatus according to the invention wherein the light beams are decoupled from the at least one transmitter-optical waveguide and the decoupled light beams interact in the examination region, in particular, with the patient such that ultrasonic waves are generated in accordance with the optoacoustic effect. In other words, in particular, light beams are decoupled or transmitted into the examination region. The end of the at least one transmitter-optical waveguide facing toward the examination region is transparent, in particular, for the decoupling of the light beams.

The ultrasonic imaging defines, in particular, the variant of the optical waveguide-transmitter apparatus according to the invention wherein the light beams are converted by an interaction in the optical absorption layer, so that ultrasonic waves are generated which are decoupled into the examination region, wherein these ultrasonic waves interact with the patient in the examination region such that ultrasonic waves are reflected by the patient. In other words, in particular, ultrasonic waves are decoupled or transmitted into the examination region. The optical absorption layer can have, in particular, a metal, for example, gold.

The optical waveguide-transmitter apparatus can have, in particular, a plurality of transmitter-optical waveguides in a quantity N=2x, where x>0, which are all configured for optoacoustic imaging or all for ultrasonic imaging or partially for optoacoustic imaging and partially for ultrasonic imaging. The plurality of optical waveguides can, in principle, guide the light beams simultaneously, in particular if a wavelength of the light beams in the optical waveguides differs. In this case, the light beams are separated and/or acquired via a filter and/or a spectral photodetector. One embodiment provides that the at least one transmitter-optical waveguide is configured for optoacoustic imaging of the examination region and a further transmitter-optical waveguide of the optical waveguide-transmitter apparatus is configured for ultrasonic imaging. This embodiment is advantageous, in particular, since a combination of the optoacoustic imaging with the ultrasonic imaging is enabled which can differ, for example, in a frequency and/or a bandwidth of the generated ultrasonic waves and has the advantages of both imaging types in an optical waveguide-transmitter apparatus with a small structure.

One embodiment provides, that the optical waveguide-transmitter apparatus has a multiplexer for multiplexing the light beams guided in at least one transmitter-optical waveguide. This embodiment is particularly advantageous if the optical waveguide-transmitter apparatus has the plurality of transmitter-optical waveguides. In this case, the light beams of the plurality of transmitter-optical waveguides can be guided in a number of fibers that is smaller than the number of the plurality of transmitter-optical waveguides. The multiplexer typically connects the plurality of transmitter-optical waveguides to the at least one fiber.

One embodiment provides that the light beams are laser beams, in particular, with a wavelength between 300 nm and 2000 nm. For example, the laser beams have a wavelength between 600 nm and 1000 nm for the optoacoustic imaging and/or preferably between 1300 nm and 1600 nm for the ultrasonic imaging.

One embodiment provides that the carrier layer at least in sections surrounds the longitudinal sides of the at least one transmitter-optical waveguide. In this case, the at least one transmitter-optical waveguide, in particular, is completely surrounded by the carrier layer at least on a longitudinal portion.

The ultrasonic transceiver apparatus according to at least one embodiment of the invention comprises the optical waveguide-transmitter apparatus and an ultrasonic receiver-optical waveguide for receiving ultrasonic waves reflected in the examination region, wherein at least one longitudinal side of the ultrasonic receiver-optical waveguide is at least partially surrounded by the carrier layer of the optical waveguide-transmitter apparatus. This embodiment is particularly advantageous since an integration of the at least one transmitter-optical waveguide and of the ultrasonic receiver-optical waveguide is enabled on the carrier layer, in particular, on the "semiconductor material on an insulator" platform.

The ultrasonic receiver-optical waveguide can be configured, in particular, according to the scientific publication by Shnaiderman et al. In this embodiment, the ultrasonic receiver-optical waveguide has a metallic reflection layer, a first Bragg grating with a grating period, a second Bragg grating with the grating period and a discontinuous portion between the first Bragg grating and the second Bragg grating. The grating period relates, in particular, to the regular corrugations introduced into the ultrasonic receiver-optical waveguide in order to form the first Bragg grating and the second Bragg grating. The grating period of the first Bragg grating and of the second Bragg grating is broken down, in particular, in the discontinuous portion. The metallic reflection layer and the first Bragg grating together form, in particular, a first optical mirror and the second Bragg grating forms a second optical mirror. The metallic reflection layer comprises, in particular, gold.

By way of example, along an optical axis of the ultrasonic receiver-optical waveguide, an extent of the metallic reflection layer can be 100 nm, an extent of the first Bragg grating can be 20 μm and an extent of the second Bragg grating can be 125 μm. For example, a first end of the ultrasonic receiver-optical waveguide can be abraded far enough so that the extent of the first Bragg grating is equal to or smaller than the grating period of the second Bragg grating. The abraded end is completed, in particular, with the metallic reflection layer. Typically, the first Bragg grating is as short as possible so that the discontinuous portion of the metallic reflection layer is as close as possible without damaging the discontinuous portion during production. By this means, a sensitivity of the ultrasonic receiver-optical waveguide is advantageously increased. Typically, the extent of the first Bragg grating and the extent of the second Bragg grating are mutually different. In particular, the extent of the first Bragg grating is shorter than the extent of the second Bragg grating. The extent of the discontinuous portion is typically different as compared with half the grating period, in particular, shorter than half the grating period. The extents described above depend, in particular, upon a wavelength and/or a bandwidth of the light beams and can therefore vary. In this case, in particular, the first end of the ultrasonic receiver-optical waveguide is oriented toward the examination region.

Ultrasonic waves reflected in the examination region which impinge upon the metallic reflection layer shift, in particular, a wavelength and/or an intensity of further light beams guided in the ultrasonic receiver-optical waveguide. These modified light beams can be detected in a photodetector of a control device and reconstructed into an image.

One embodiment provides that the ultrasonic transceiver apparatus has a screening element which is arranged in a region between the end of the at least one transmitter-optical waveguide facing toward the examination region and an end of the ultrasonic receiver-optical waveguide facing toward the examination region. The screening element is, in particular, a collimator, a grating or a gradient index lens. This embodiment is advantageous, in particular, since ultrasonic waves to be coupled in or decoupled can be separated between the different optical waveguides.

One embodiment provides that the ultrasonic transceiver apparatus has a third optical waveguide which is configured as a further transmitter-optical waveguide, wherein the ultrasonic receiver-optical waveguide is arranged between the at least one transmitter-optical waveguide and the third optical waveguide, or wherein the third optical waveguide is configured as a further ultrasonic receiver-optical waveguide, wherein the at least one transmitter-optical waveguide is arranged between the ultrasonic receiver-optical waveguide and the third optical waveguide. The at least one transmitter-optical waveguide, the ultrasonic receiver-optical waveguide and the third optical waveguide are preferably arranged alternatingly, for example, such that between two transmitter-optical waveguides, in each case, a receiver-optical waveguide is provided or between two receiver-optical waveguides, a transmitter-optical waveguide is provided in each case. By this means, a spatial resolution of the ultrasonic transceiver apparatus can be improved.

One embodiment provides that the ultrasonic transceiver apparatus has an additional optical waveguide, wherein the at least one transmitter-optical waveguide, the ultrasonic receiver-optical waveguide and the additional optical waveguide are arranged two-dimensionally with respect to the examination region. The at least one transmitter-optical waveguide, the ultrasonic receiver-optical waveguide and the additional optical waveguide are preferably arranged in a grid pattern. In combination with the previous embodiment, the optical waveguides can be arranged, in particular, in a chessboard pattern. This embodiment enables, in particular, a two-dimensional imaging, whereby the ultrasonic transceiver apparatus typically has to be moved less.

An ultrasonic imaging apparatus according to at least one embodiment of the invention comprises the optical waveguide-transmitter apparatus or the ultrasonic transceiver apparatus, a control apparatus and a light source apparatus, wherein the light source apparatus is connected via at least one fiber to the at least one transmitter-optical waveguide and wherein the control apparatus is configured for an actuation of the light source apparatus such that the at least one transmitter-optical waveguide guides the light beams during operation. The light source apparatus can comprise an LED or a laser. The at least one fiber can be a glass fiber. The at least one fiber is, for example, attached to a second end of the at least one transmitter-optical waveguide, the end lying opposite the end facing toward the examination region, for example, via an interface, in particular, via an optical coupler and/or via the multiplexer.

An inventive method of at least one embodiment is for producing the optical waveguide-transmitter apparatus comprises, wherein a substrate made of a semiconductor material is provided, a carrier layer is arranged on the substrate and at least one transmitter-optical waveguide is mounted on the carrier layer such that at least one longitudinal side of the at least one transmitter-optical waveguide is at least partially surrounded by the carrier layer. In the manufacturing method, for example, a wafer is processed via ultraviolet radiation or electron-beam lithography such that the at least one optical waveguide can guide the light beams in the optical waveguide-transmitter apparatus.

Features, advantages or alternative embodiments mentioned in the description of the apparatus are also transferable similarly to the method and vice versa. In other words, claims for the method can be developed with features of the apparatus and vice versa. In particular, the apparatus according to the invention can be used in the method.

FIG. 1 shows the optical waveguide-transmitter apparatus 10 with a first cross-section perpendicular to an optical axis of the light beams. The optical axis is parallel to the z-axis in this example embodiment.

The optical waveguide-transmitter apparatus 10 for imaging an examination region U with ultrasonic waves generated by way of light beams has a substrate 11 made of a semiconductor material, a carrier layer 12 arranged on the substrate 11 and at least one transmitter-optical waveguide 13 made of a semiconductor material with a refractive index greater than a refractive index of the carrier layer 12. A longitudinal side 13.L1 of the at least one transmitter-optical waveguide 13 is at least partially surrounded by the carrier layer 12.

The transmitter-optical waveguide 13 in this example embodiment has a pyramid-shaped or multi-stepped cross-section and is configured for guiding the light beams.

The transmitter-optical waveguide 13 is configured at an end 13.E facing toward the examination region U for a decoupling of the light beams in the examination region U for generating the ultrasonic waves in the examination region U by way of the decoupled light beams for an optoacoustic imaging.

Alternatively, the transmitter-optical waveguide 13 can have, at the end 13.E facing toward the examination region, an optical absorption layer 14 (not shown in FIG. 1) for such a conversion of the light beams so that in the examination region U, the ultrasonic waves generated are decoupled for an ultrasonic imaging.

Figure 2:
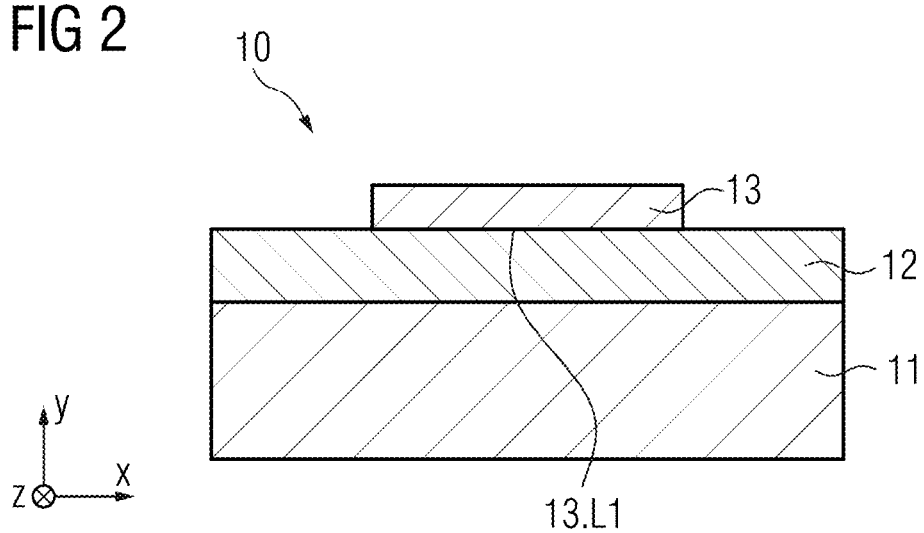

FIG. 2 shows the optical waveguide-transmitter apparatus 10 with a second cross-section perpendicular to the optical axis of the light beams.

In this embodiment, the transmitter-optical waveguide 13 has a rectangular cross-section, wherein the longitudinal side 13.L1 of the at least one transmitter-optical waveguide 13 is at least partially surrounded by the carrier layer 12.

FIG. 3 shows the optical waveguide-transmitter apparatus 10 with a third cross-section perpendicular to the optical axis of the light beams.

In this embodiment, the transmitter-optical waveguide 13 has a rectangular cross-section, wherein the longitudinal sides 13.L1, 13.L2, 13.L3 of the at least one transmitter-optical waveguide 13 are at least partially surrounded by the carrier layer 12.

FIG. 4 shows the optical waveguide-transmitter apparatus 10 with a third cross-section perpendicular to the optical axis of the light beams.

In this embodiment, the transmitter-optical waveguide 13 has a rectangular cross-section, wherein the longitudinal sides 13.L1, 13.L2, 13.L3, 13.L4 of the at least one transmitter-optical waveguide 13 are at least partially surrounded by the carrier layer 12.

The example embodiments shown in FIGS. 1 to 4 differ substantially in the cross-section of the at least one transmitter-optical waveguide 13 and/or a number of longitudinal sides 13.L1, 13.L2, 13.L3, 13.L4, which are at least partially surrounded by the carrier layer.

In addition, the light beams can optionally be laser beams. The semiconductor material comprises silicon, germanium, gallium, phosphorus, Ti: LiNbO$_3$ and/or antimony.

Figure 5:
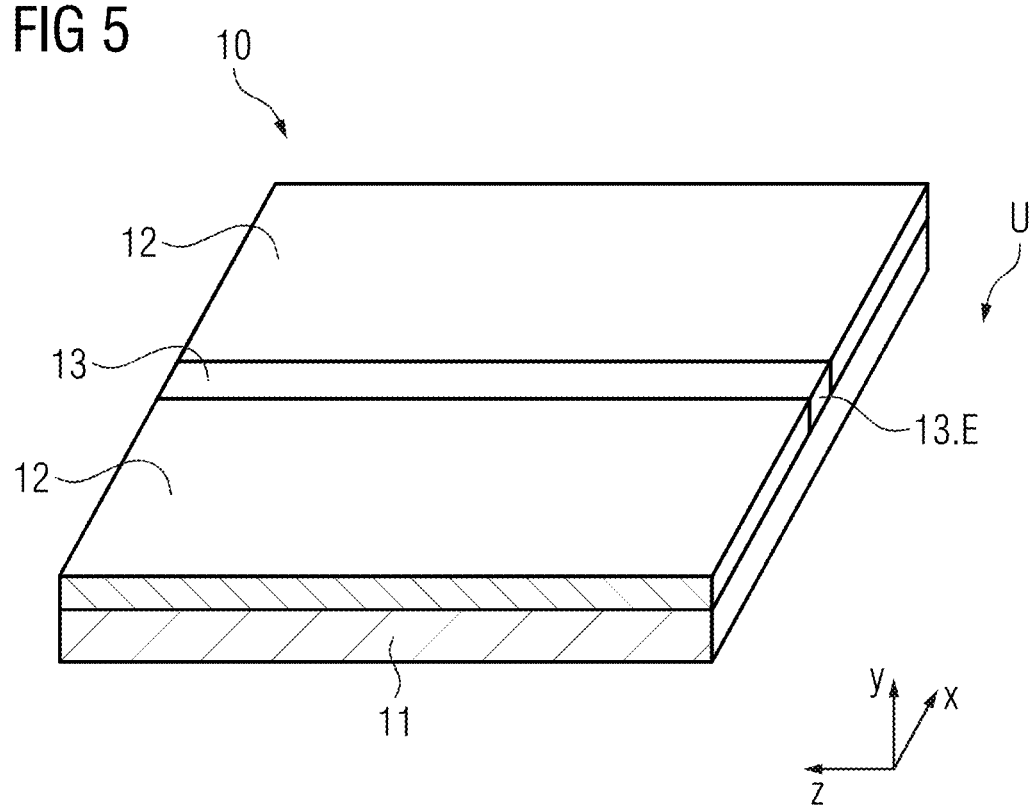
FIG. 5 is the optical waveguide-transmitter apparatus 10 in an embodiment for optoacoustic imaging.

FIG. 5 shows the optical waveguide-transmitter apparatus 10 in an embodiment for optoacoustic imaging in a perspective view. The embodiment of the optical waveguide-transmitter apparatus 10 comprises three longitudinal sides 13.L1, 13.L2, 13.L3, which are surrounded by the carrier layer 12. The at least one transmitter-optical waveguide 13 is substantially embedded in the carrier layer 12. An end 13.E facing toward the examination region U is configured for a decoupling of the light beams in the examination region U for generating the ultrasonic waves in the examination region U by way of the decoupled light beams.

Figure 6:
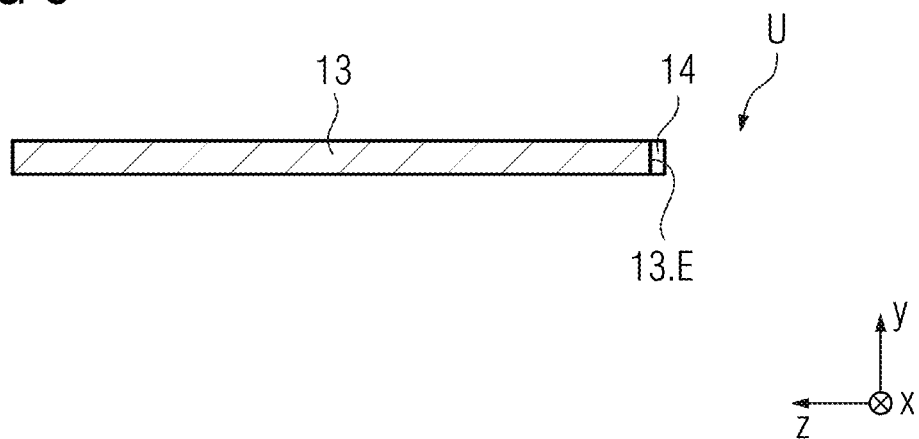
FIG. 6 is the optical waveguide-transmitter apparatus 10 in an embodiment for ultrasonic imaging.

FIG. 6 shows the optical waveguide-transmitter apparatus 10 in an embodiment for ultrasonic imaging in a side view. For reasons of clarity, FIG. 6 shows only the at least one transmitter-optical waveguide 13 and the optical absorption layer 14 in a section along the optical axis. The example embodiment of FIG. 6 differs in this case substantially in the optical absorption layer 14 from the example embodiment of FIG. 5. In addition, a wavelength and/or a bandwidth of the light beams can differ.

The at least one transmitter-optical waveguide 13 has, at the end 13.E facing toward the examination region U, the optical absorption layer 14 for such a conversion of the light beams so that in the examination region U, the ultrasonic waves generated are decoupled for an ultrasonic imaging. By the preferably seamless joining of the optical absorption layer 14 to the end 13.E, the embodiment shown in FIG. 5 for optoacoustic imaging can, in principle, be developed to the embodiment for the ultrasonic imaging according to FIG. 6.

Figure 7:
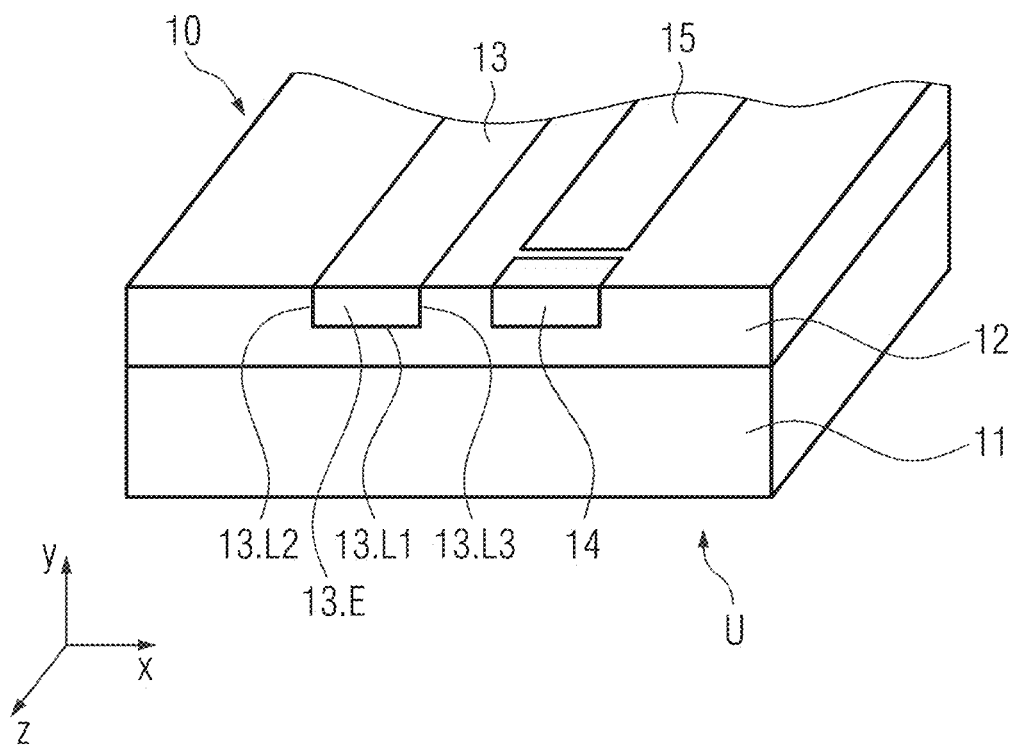
FIG. 7 is the optical waveguide-transmitter apparatus 10 in an embodiment for optoacoustic and ultrasonic imaging.

FIG. 7 shows a further embodiment of the optical waveguide-transmitter apparatus 10 in a perspective view.

The at least one transmitter-optical waveguide 13 is configured for optoacoustic imaging of the examination region U. A further transmitter-optical waveguide 15 of the optical waveguide-transmitter apparatus 10 is configured for ultrasonic imaging and, for this purpose, has the optical absorption layer 14 at one end of the further transmitter-optical waveguide 15. A gap shown in FIG. 7 along the optical axis of the further transmitter-optical waveguide 15 between the optical absorption layer 14 and the further transmitter-optical waveguide serves merely for greater clarity. Preferably, the optical absorption layer 14 directly adjoins the further transmitter-optical waveguide 15.

It is conceivable, in principle, that both transmitter-optical waveguides 13, 15 are configured for optoacoustic imaging or ultrasonic imaging.

At both the ends (not shown) of the transmitter-optical waveguide 13, 15, a multiplexer (not shown) can be arranged for multiplexing the light beams guided in at least one transmitter-optical waveguide 13, 15, and/or an optical coupler in order to connect the optical waveguides 13, 15 to a light source apparatus.

Figure 8:
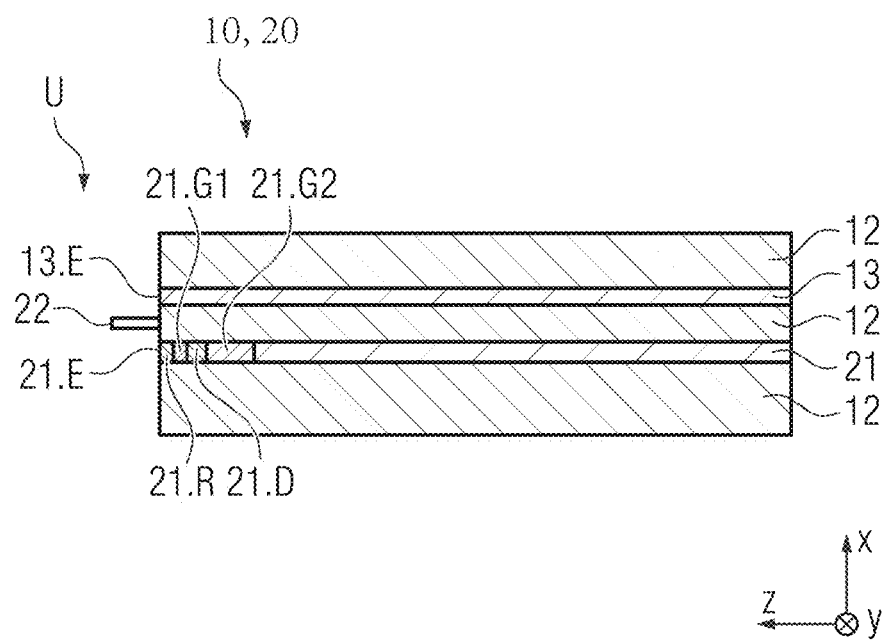
FIG. 8 is an ultrasonic transceiver apparatus 20.

FIG. 8 shows a plan view of an ultrasonic transceiver apparatus 20 for optoacoustic imaging.

The ultrasonic transceiver apparatus 20 has an optical waveguide-transmitter apparatus 10 and an ultrasonic receiver-optical waveguide 21. The ultrasonic receiver-optical waveguide 21 is configured for receiving ultrasonic waves reflected in the examination region U. At least one longitudinal side of the ultrasonic receiver-optical waveguide 21 is at least partially surrounded by the carrier layer 12 of the optical waveguide-transmitter apparatus 10. The ultrasonic receiver-optical waveguide 21 has a metallic reflection layer 21.R, a first Bragg grating 21.G1 with a grating period, a second Bragg grating 21.G2 with the grating period and a discontinuous portion 21.D between the first Bragg grating 21.G1 and the second Bragg grating 21.G2.

In this example embodiment, the ultrasonic transceiver apparatus 20 additionally has an optional screening element 22 which is arranged in a region between the end 13.E of the at least one transmitter-optical waveguide 13 facing toward the examination region U and an end 21.E of the ultrasonic receiver-optical waveguide 21 facing toward the examination region U. The screening element 22 is advantageous, in particular, if in a further development of FIG. 8, the ultrasonic transceiver apparatus 20 is configured for ultrasonic imaging.

Figure 9:
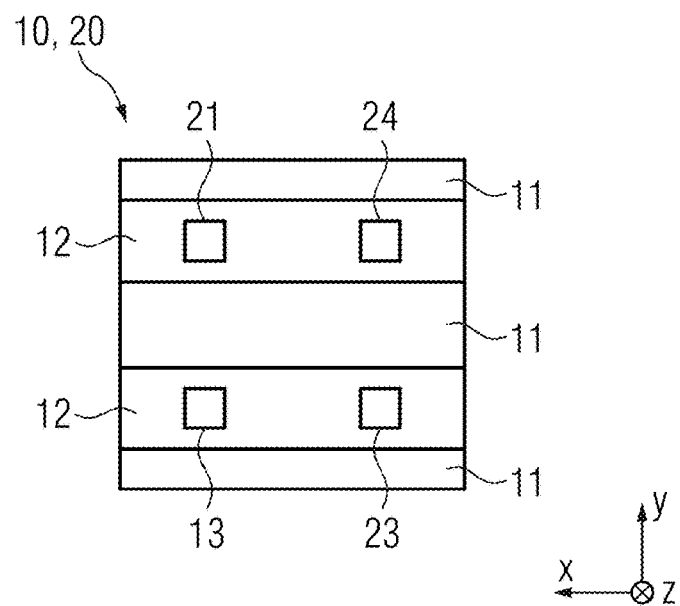
FIG. 9 is an arrangement of a plurality of optical waveguides.

FIG. 9 shows an, in particular, chessboard arrangement of a plurality of optical waveguides 13, 21, 23, 24. FIG. 9 shows an end side of the plurality of optical waveguides 13, 21, 23, 24 starting from the examination region U.

This example embodiment illustrates an embodiment wherein the ultrasonic transceiver apparatus 20 has an additional optical waveguide 24, wherein the at least one transmitter-optical waveguide 13, the ultrasonic receiver-optical waveguide 21 and the additional optical waveguide 24 are arranged two-dimensionally with respect to the examination region U and therefore do not lie on a line. In addition, this example embodiment provides that the ultrasonic transceiver apparatus 20 has a third optical waveguide 24 which is configured as a further transmitter-optical waveguide and, in this example embodiment, corresponds to the additional optical waveguide 24, wherein the ultrasonic receiver-optical waveguide 21 is arranged between the at least one transmitter-optical waveguide 13 and the third optical waveguide 24. In this example embodiment, it is shown that the alternating arrangement "between" also comprises a variant in a triangular form in addition to the variant along one direction.

In addition, this example embodiment shows that the third optical waveguide 23 is configured as a further ultrasonic receiver-optical waveguide, wherein the at least one transmitter-optical waveguide 13 is arranged between the ultrasonic receiver-optical waveguide 21 and the third optical waveguide 23.

Alternatively to the chessboard-like arrangement in FIG. 9, the plurality of optical waveguides 13, 21, 23, 24 can be stacked over one another linearly separated according to transmitter or receiver.

Figure 10:
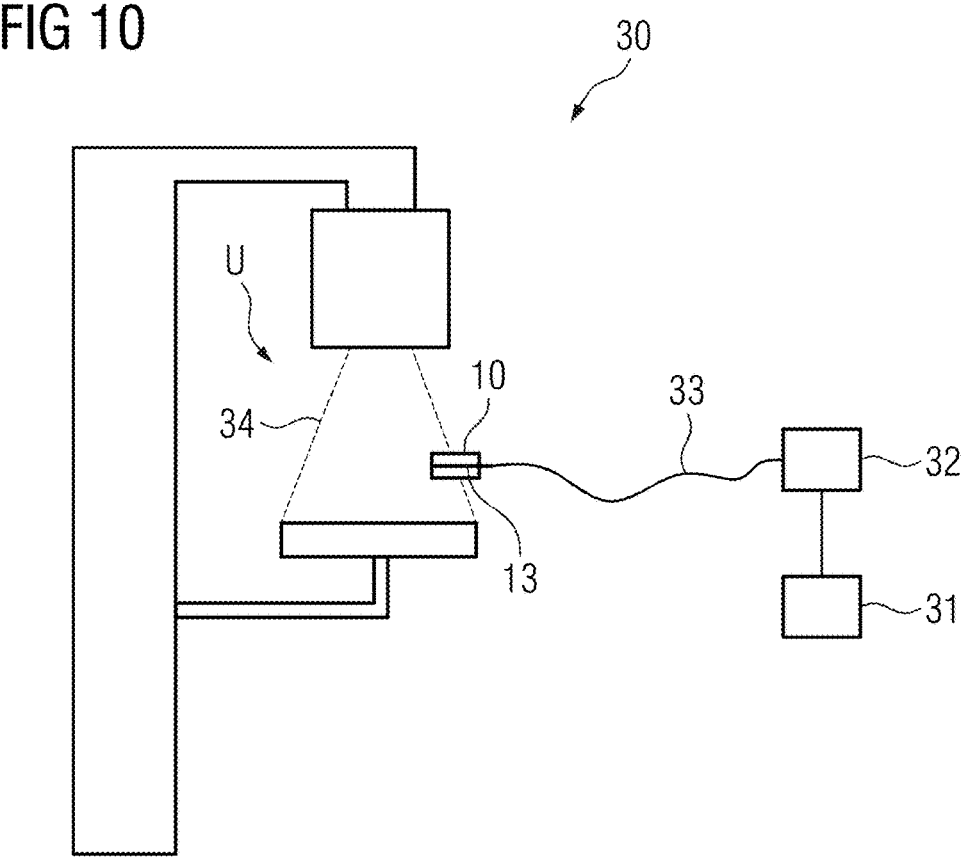
FIG. 10 is an ultrasonic imaging apparatus 30.

FIG. 10 shows an ultrasonic imaging apparatus 30. The ultrasonic imaging apparatus 30 has the optical waveguide-transmitter apparatus 10, a control apparatus 31 and a light source apparatus 32. The light source apparatus 32 is connected via at least one fiber 33 to the at least one transmitter-optical waveguide 13. The control apparatus 31 is configured for controlling the light source apparatus 32 such that the at least one transmitter-optical waveguide 13 guides the light beams during operation.

The ultrasonic imaging apparatus 30 with the optical waveguide-transmitter apparatus 10 is arranged in an X-ray beam path 34 of an X-ray device. The X-ray beam path 34 is situated between an X-ray tube and an X-ray detector and comprises at least partially the examination region U. The X-ray device can be a mammography device or a computed tomography device. Alternatively, the optical waveguide-transmitter apparatus can be arranged in a main magnetic field of a magnetic resonance tomograph.

The light beams are coupled into the at least one transmitter-optical waveguide 13 via the at least one fiber 33 from the light source apparatus 32. If, in a development, the ultrasonic imaging apparatus 30 has the ultrasonic receiver-optical waveguide 21, the control apparatus 31 is preferably configured to couple further light beams into the ultrasonic receiver-optical waveguide 21 via the at least one fiber 33 from the light source apparatus 32. In addition, the control device 31 is preferably configured to decouple received phase-shifted light beams from the at least one fiber 33 in the ultrasonic receiver-optical waveguide 21 dependent upon the ultrasonic waves reflected from the examination region U and to reconstruct them into an image.

In an advantageous embodiment, the light source apparatus 32 has a laser, so that the light beams are laser beams.

Although the invention has been illustrated and described in detail with the preferred example embodiments, the invention is nevertheless not restricted by the examples given and other variations can be derived therefrom by a person skilled in the art without departing from the protective scope of the invention.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An optical waveguide-transmitter apparatus for imaging an examination region via ultrasonic waves generated by light beams, comprising:
   a substrate, the substrate including a first semiconductor material;
   a carrier layer, the carrier layer being on the substrate;
   at least one transmitter-optical waveguide, the at least one transmitter-optical waveguide including a second semiconductor material with a refractive index greater than a refractive index of the carrier layer, and the at least one transmitter-optical waveguide including at least one longitudinal side surrounded by the carrier layer; and
   a further transmitter-optical waveguide, the further transmitter-optical waveguide including at least one longitudinal side surrounded by the carrier layer,
   wherein the at least one transmitter-optical waveguide and the further transmitter-optical waveguide are configured to guide the light beams simultaneously,
   the at least one transmitter-optical waveguide includes an optical absorption layer configured to convert the light beams to generate ultrasonic waves which are decoupled into the examination region for an ultrasonic imaging process, the optical absorption layer being at an end of the at least one transmitter-optical waveguide facing toward the examination region, and
   the further transmitter-optical waveguide is configured for an optoacoustic imaging process.

2. The optical waveguide-transmitter apparatus of claim 1, wherein the light beams are laser beams.

3. The optical waveguide-transmitter apparatus of claim 1, wherein:
   the further transmitter-optical waveguide including an end configured to decouple the light beams into the examination region for generating the ultrasonic waves in the examination region by way of the decoupled light beams for the optoacoustic imaging process.

4. The optical waveguide-transmitter apparatus of claim 1, wherein the first semiconductor material and the second semiconductor material include at least one of silicon, germanium, gallium, phosphorus, Ti:LiNbO$_3$ or antimony.

5. The optical waveguide-transmitter apparatus of claim 1, wherein the carrier layer surrounds each longitudinal side of at least one section of the at least one transmitter-optical waveguide.

6. The optical waveguide-transmitter apparatus of claim 1, further comprising:
   a multiplexer, the multiplexer being configured to multiplex the light beams guided in the at least one transmitter-optical waveguide.

7. An ultrasonic transceiver apparatus, comprising:
the optical waveguide-transmitter apparatus of claim 1; and
an ultrasonic receiver-optical waveguide configured to receive the ultrasonic waves reflected in the examination region, the ultrasonic receiver-optical waveguide including at least one longitudinal side at least partially surrounded by the carrier layer of the optical waveguide-transmitter apparatus.

8. The ultrasonic transceiver apparatus of claim 7, further comprising:
a screening element in a region between the end of the at least one transmitter-optical waveguide facing toward the examination region and an end of the ultrasonic receiver-optical waveguide facing toward the examination region.

9. The ultrasonic transceiver apparatus of claim 7, wherein the ultrasonic receiver-optical waveguide includes,
a metallic reflection layer,
a first Bragg grating with a grating period,
a second Bragg grating with the grating period, and
a discontinuous portion between the first Bragg grating and the second Bragg grating.

10. The ultrasonic transceiver apparatus of claim 7, wherein
the ultrasonic receiver-optical waveguide is between the at least one transmitter-optical waveguide and the further transmitter-optical waveguide, and the ultrasonic transceiver apparatus further comprises:
a further ultrasonic receiver-optical waveguide, the at least one transmitter-optical waveguide being between the ultrasonic receiver-optical waveguide and the further ultrasonic receiver-optical waveguide.

11. The ultrasonic transceiver apparatus of claim 7,
wherein the at least one transmitter-optical waveguide, the ultrasonic receiver-optical waveguide and the further transmitter-optical waveguide are arranged two-dimensionally with respect to the examination region.

12. An ultrasonic imaging apparatus, comprising:
the ultrasonic transceiver apparatus of claim 7;
a control apparatus; and
a light source apparatus, the light source apparatus being connected, via at least one fiber, to the at least one transmitter-optical waveguide, wherein
the control apparatus is configured to actuate the light source apparatus to enable the at least one transmitter-optical waveguide to guide the light beams during operation of the ultrasonic imaging apparatus.

13. The ultrasonic imaging apparatus of claim 12, wherein the light source apparatus includes a laser.

14. An arrangement of the optical waveguide-transmitter apparatus of claim 1 in a main magnetic field of a magnetic resonance tomograph or in an X-ray beam path of an X-ray device.

15. A method for producing an optical waveguide-transmitter apparatus, comprising:
providing a substrate including a semiconductor material;
arranging a carrier layer on the substrate; and
mounting at least one transmitter-optical waveguide on the carrier layer such that at least one longitudinal side of the at least one transmitter-optical waveguide is at least partially surrounded by the carrier layer.

16. The optical waveguide-transmitter apparatus of claim 2, wherein:
the further transmitter-optical waveguide including an end configured to decouple the light beams into the examination region for generating the ultrasonic waves in the examination region by way of the decoupled light beams for the optoacoustic imaging process.

17. The optical waveguide-transmitter apparatus of claim 2, wherein the first semiconductor material and the second semiconductor material include at least one of silicon, germanium, gallium, phosphorus, Ti:LiNbO$_3$ or antimony.

18. The optical waveguide-transmitter apparatus of claim 2, further comprising:
a multiplexer, the multiplexer being configured to multiplex the light beams guided in the at least one transmitter-optical waveguide.

19. An ultrasonic transceiver apparatus, comprising:
the optical waveguide-transmitter apparatus of claim 2; and
an ultrasonic receiver-optical waveguide to receive ultrasonic waves reflected in the examination region, the ultrasonic receiver-optical waveguide including at least one longitudinal side at least partially surrounded by the carrier layer of the optical waveguide-transmitter apparatus.

20. The ultrasonic transceiver apparatus of claim 8, wherein the ultrasonic receiver-optical waveguide includes,
a metallic reflection layer,
a first Bragg grating with a grating period,
a second Bragg grating with the grating period, and
a discontinuous portion between the first Bragg grating and the second Bragg grating.

21. The ultrasonic transceiver apparatus of claim 8, wherein
the ultrasonic receiver-optical waveguide is between the at least one transmitter-optical waveguide and the further transmitter-optical waveguide, and the ultrasonic transceiver apparatus further comprises:
a further ultrasonic receiver-optical waveguide, the at least one transmitter-optical waveguide being between the ultrasonic receiver-optical waveguide and the further ultrasonic receiver-optical waveguide.

22. The ultrasonic transceiver apparatus of claim 9, wherein
the ultrasonic receiver-optical waveguide is being between the at least one transmitter-optical waveguide and the further transmitter-optical waveguide, and the ultrasonic transceiver apparatus further comprises:
a further ultrasonic receiver-optical waveguide, the at least one transmitter-optical waveguide being between the ultrasonic receiver-optical waveguide and the further ultrasonic receiver-optical waveguide.

23. An ultrasonic imaging apparatus, comprising:
the ultrasonic transceiver apparatus of claim 8;
a control apparatus; and
a light source apparatus, the light source apparatus being connected, via at least one fiber, to the at least one transmitter-optical waveguide, wherein
the control apparatus is configured to actuate the light source apparatus to enable the at least one transmitter-optical waveguide to guide the light beams during operation of the ultrasonic imaging apparatus.

24. An ultrasonic imaging apparatus, comprising:
the ultrasonic transceiver apparatus of claim 9;
a control apparatus; and
a light source apparatus, the light source apparatus being connected, via at least one fiber, to the at least one transmitter-optical waveguide, wherein
the control apparatus is configured to actuate the light source apparatus to enable the at least one transmitter-optical waveguide to guide the light beams during operation of the ultrasonic imaging apparatus.

25. The optical waveguide-transmitter apparatus of claim 1, wherein the at least one transmitter-optical waveguide is embedded in the carrier layer.

* * * * *